(12) United States Patent
Chen et al.

(10) Patent No.: US 12,023,524 B2
(45) Date of Patent: Jul. 2, 2024

(54) NEUTRON CAPTURE THERAPY SYSTEM COMPRISING A BEAM-SHAPING ASSEMBLY HAVING A MODERATOR AND A FRAME ACCOMMODATING THE MODERATOR

(71) Applicant: NEUBORON THERAPY SYSTEM LTD., Fujian (CN)

(72) Inventors: Wei-Lin Chen, Jiangsu (CN); Tao Jiang, Jiangsu (CN)

(73) Assignee: NEUBORON THERAPY SYSTEM LTD., Fujian (CN)

( * ) Notice: Subject to any disclaimer, the term of this patent is extended or adjusted under 35 U.S.C. 154(b) by 324 days.

(21) Appl. No.: 17/494,876

(22) Filed: Oct. 6, 2021

(65) Prior Publication Data
US 2022/0080225 A1    Mar. 17, 2022

Related U.S. Application Data

(63) Continuation of application No. PCT/CN2020/079731, filed on Mar. 17, 2020.

(30) Foreign Application Priority Data

Apr. 17, 2019 (CN) .......................... 201910308038.8

(51) Int. Cl.
*A61N 5/10* (2006.01)
*G21G 4/02* (2006.01)
(Continued)

(52) U.S. Cl.
CPC .............. *A61N 5/1077* (2013.01); *A61N 5/10* (2013.01); *A61N 5/1048* (2013.01);
(Continued)

(58) Field of Classification Search
CPC ...... A61N 5/10; A61N 5/1048; A61N 5/1049; A61N 5/1064; A61N 5/1065;
(Continued)

(56) References Cited

U.S. PATENT DOCUMENTS 9,789,340 B2 * 10/2017 Liu ...................... A61N 5/1077
9,889,320 B2 *  2/2018 Liu .......................... G21K 1/10
(Continued)

FOREIGN PATENT DOCUMENTS

CN    104771837 A    7/2015
CN    205334975 U    6/2016
(Continued)

OTHER PUBLICATIONS

International Search Report of PCT/CN2020/079731, Jun. 15, 2020.

*Primary Examiner* — Allen C. Ho
(74) *Attorney, Agent, or Firm* — Locke Lord LLP; Tim Tingkang Xia, Esq.

(57) ABSTRACT

A neutron capture therapy system may prevent deformation and damage of a material of a beam shaping assembly (20), thereby improving flux and quality of a neutron source. A boron neutron capture therapy system (100) includes a neutron generating device (10) and a beam shaping assembly (20), where the neutron generating device (10) includes an accelerator (11) and a target (T), a charged particle beam (P) generated by acceleration of the accelerator (11) interacts with the target (T) to generate neutrons, the neutrons form a neutron beam (N), the neutron beam (N) defines a main axis (X); the beam shaping assembly (20) includes a moderator (231), a reflector (232), and a radiation shield (233); and the beam shaping assembly (20) further includes a frame (21) accommodating the moderator (231).

20 Claims, 6 Drawing Sheets

(51) Int. Cl.
*G21K 1/02* (2006.01)
*G21K 5/02* (2006.01)

(52) U.S. Cl.
CPC ......... *A61N 5/1065* (2013.01); *A61N 5/1078* (2013.01); *G21G 4/02* (2013.01); *G21K 1/02* (2013.01); *G21K 5/02* (2013.01); *A61N 2005/1087* (2013.01); *A61N 2005/109* (2013.01); *A61N 2005/1094* (2013.01)

(58) Field of Classification Search
CPC .. A61N 5/1067; A61N 5/1071; A61N 5/1077; A61N 5/1078; A61N 5/1079; A61N 2005/1085; A61N 2005/1087; A61N 2005/1089; A61N 2005/109; G21G 4/00; G21G 4/02; G21K 1/02; G21K 1/025
USPC .................... 250/493.1; 378/64, 65
See application file for complete search history.

(56) References Cited

U.S. PATENT DOCUMENTS

| | | | | |
|---|---|---|---|---|
| 10,157,693 B2* | 12/2018 | Liu | .............. | A61N 5/10 |
| 10,328,286 B2* | 6/2019 | Liu | .............. | C04B 35/6455 |
| 10,434,333 B2* | 10/2019 | Liu | .............. | A61N 5/1077 |
| 10,462,893 B2* | 10/2019 | Park, Jr. | .............. | G21G 4/02 |
| 10,537,750 B2* | 1/2020 | Liu | .............. | A61N 5/1049 |
| 10,556,127 B2* | 2/2020 | Liu | .............. | A61N 5/1082 |
| 10,639,499 B2* | 5/2020 | Liu | .............. | G21K 1/10 |
| 10,744,345 B2* | 8/2020 | Liu | .............. | A61N 5/1042 |
| 10,773,104 B2* | 9/2020 | Liu | .............. | H05H 3/06 |
| 10,898,731 B2* | 1/2021 | Liu | .............. | A61N 5/1077 |
| 10,898,733 B2* | 1/2021 | Liu | .............. | A61N 5/1081 |
| 10,926,108 B2* | 2/2021 | Liu | .............. | A61N 5/1042 |
| 10,926,110 B2* | 2/2021 | Liu | .............. | A61N 5/1049 |
| 10,994,154 B2* | 5/2021 | Liu | .............. | B33Y 80/00 |
| 11,024,437 B2* | 6/2021 | Park, Jr. | .............. | G21G 1/10 |
| 11,058,898 B2* | 7/2021 | Liu | .............. | A61N 5/1064 |
| 11,198,023 B2* | 12/2021 | Chen | .............. | G21K 5/04 |
| 11,224,766 B2* | 1/2022 | Liu | .............. | G21K 5/04 |
| 11,266,859 B2* | 3/2022 | Liu | .............. | H05H 3/06 |
| 11,338,155 B2* | 5/2022 | Hsiao | .............. | H05H 3/06 |
| 11,400,314 B2* | 8/2022 | Hsiao | .............. | H05H 3/06 |
| 11,400,316 B2* | 8/2022 | Liu | .............. | A61N 5/10 |
| 11,458,336 B2* | 10/2022 | Tsai | .............. | A61N 5/1067 |
| 11,559,705 B2* | 1/2023 | Chen | .............. | A61K 41/0095 |
| 11,561,308 B2* | 1/2023 | Liu | .............. | A61N 5/1075 |
| 11,740,370 B2* | 8/2023 | Liu | .............. | H05H 3/06 250/391 |
| 11,813,483 B2* | 11/2023 | Liu | .............. | A61N 5/1078 |
| 11,826,583 B2* | 11/2023 | Jiang | .............. | A61N 5/1078 |
| 2012/0330084 A1 | 12/2012 | Pantell et al. | | |
| 2018/0193673 A1 | 7/2018 | Liu et al. | | |

FOREIGN PATENT DOCUMENTS

| | | |
|---|---|---|
| CN | 107802968 A | 3/2018 |
| CN | 106552322 B | 8/2018 |
| CN | 108926784 A | 12/2018 |
| CN | 208335758 U | 1/2019 |
| CN | 208372315 U | 1/2019 |
| EP | 3456382 A1 | 3/2019 |
| JP | 2006047115 A | 2/2006 |
| JP | 5429053 B2 | 2/2014 |
| JP | 2014115122 A | 6/2014 |
| JP | 2018161449 A | 10/2018 |
| JP | 2018535717 A | 12/2018 |
| WO | 2013124975 A1 | 8/2013 |
| WO | 2017164408 A1 | 9/2017 |

* cited by examiner

NEUTRON CAPTURE THERAPY SYSTEM COMPRISING A BEAM-SHAPING ASSEMBLY HAVING A MODERATOR AND A FRAME ACCOMMODATING THE MODERATOR

CROSS-REFERENCE TO RELATED PATENT APPLICATION

This application is a continuation application of International Application No. PCT/CN2020/079731, filed on Mar. 17, 2020, which claims priority to Chinese Patent Application No. 201910308038.8, filed on Apr. 17, 2019, the disclosures of which are hereby incorporated by reference.

FIELD

The present disclosure relates to a radiation irradiation system, and in particular to a neutron capture therapy system.

BACKGROUND

The background description provided herein is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

As atomics moves ahead, such radiotherapy as Cobalt-60, linear accelerators and electron beams has been one of major means to cancer therapy. However, conventional photon or electron therapy has been undergone physical restrictions of radioactive rays; for example, many normal tissues on a beam path will be damaged as tumor cells are destroyed. On the other hand, sensitivity of tumor cells to the radioactive rays differs greatly, so in most cases, conventional radiotherapy falls short of treatment effectiveness on radioresistant malignant tumors (such as glioblastoma multiforme and melanoma).

For the purpose of reducing radiation damage to the normal tissue surrounding a tumor site, target therapy in chemotherapy has been employed in the radiotherapy. While for high-radioresistant tumor cells, radiation sources with high RBE (relative biological effectiveness) including such as proton, heavy particle and neutron capture therapy have also developed. Among them, the neutron capture therapy combines the target therapy with the RBE, such as the boron neutron capture therapy (BNCT). By virtue of specific grouping of boronated pharmaceuticals in the tumor cells and precise neutron beam regulation, BNCT is provided as a better cancer therapy choice than conventional radiotherapy.

Boron Neutron Capture Therapy (BNCT) takes advantage that the boron (B-10)-containing pharmaceuticals have high neutron capture cross section and produces $^4$He and $^7$Li heavy charged particles through $^{10}$B(n,α)$^7$Li neutron capture and nuclear fission reaction. As illustrated in FIGS. 1 and 2, a schematic drawing of BNCT and a nuclear reaction formula of $^{10}$B (n,α)$^7$Li neutron capture are shown, the two charged particles, with average energy at about 2.33 MeV, are of high linear energy transfer (LET) and short-range characteristics. LET and range of the alpha particle are 150 keV/micrometer and 8 micrometers respectively while those of the heavy charged particle $^7$Li are 175 keV/micrometer and 5 micrometers respectively, and the total range of the two particles approximately amounts to a cell size. Therefore, radiation damage to living organisms may be restricted at the cells' level. only the tumor cells will be destroyed on the premise of having no major normal tissue damage.

BNCT is also well known for binary cancer therapy, for its effectiveness depending on the concentration of the boronated pharmaceuticals and the number of the thermal neutrons at the tumor site. Thus, besides development of the boronated pharmaceuticals, improvement of flux and quality of the neutron source plays a significant role in BNCT researches.

Therefore, it is necessary to propose a new technical solution to resolve the foregoing problem.

SUMMARY

To improve flux and quality of a neutron source, an aspect of the present invention provides a neutron capture therapy system, including a neutron generating device and a beam shaping assembly. The neutron generating device includes an accelerator and a target, a charged particle beam generated by acceleration of the accelerator interacts with the target to generate neutrons, the neutrons form a neutron beam, and the neutron beam defines a main axis. The beam shaping assembly includes a moderator, a reflector, and a radiation shield, the moderator is configured to moderate the neutrons generated from the target to an epithermal neutron energy region, the reflector surrounds the moderator and directs deviating neutrons back to the main axis to enhance intensity of an epithermal neutron beam, and the radiation shield is provided to shield leaking neutrons and photons so as to reduce dose to normal tissues in a non-irradiation area; and the beam shaping assembly further includes a frame accommodating the moderator. The frame positions and supports the moderator, so that flux and quality of the neutron source may be improved.

Further, the moderator is adjustable, and the frame includes a positioning member and a stopping member for fixing the moderator.

Preferably, half-lives of radioactive isotopes generated after materials of the positioning member and the stopping member are activated by the neutrons are less than 7 days.

Preferably, the materials of the positioning member and stopping member are an aluminum alloy, a titanium alloy, a lead-antimony alloy, a cobalt-free steel, carbon fibers, PEEK, or a high molecular polymer. The positioning member may conveniently adjust a size of the moderator, thereby adjusting flux of the neutron beam, and after the adjustment, the stopping member may quickly and conveniently implement encapsulation of the moderator.

Preferably, the moderator includes a basic part and a supplementary part, a material of the basic part is different from a material of the supplementary part, the frame forms at least one accommodating unit, the accommodating unit includes a first accommodating unit and a second accommodating unit that are adjacent to each other, the basic part is accommodated in the first accommodating unit and is composed of pieces and adjustable, when a number of the pieces of the basic part is reduced, the positioning member is disposed inside the first accommodating unit for supplementation, and the stopping member is provide to fix the basic part. The supplementary part may lower manufacturing costs of the moderator without exerting relatively large impact on quality of the beam. The positioning member and the stopping member may conveniently adjust the basic part of the moderator.

Further, a material of the basic part includes at least one of $D_2O$, Al, $AlF_3$, $MgF_2$, $CaF_2$, LiF, $Li_2CO_3$, or $Al_2O_3$, has a cross section for principally acting with fast neutrons but hardly acting with epithermal neutrons, and has a relatively good moderating effect. The basic part contains Li-6, and the basic part also serves as a thermal neutron absorber.

Further, a material of the supplementary part includes at least one of Zn, Mg, Al, Pb, Ti, La, Zr, Bi, or C. Selecting a material that is relatively easy to obtain as the material of the supplementary part may lower manufacturing costs of the moderator while producing a specific neutron moderating effect without exerting relatively large impact on quality of the beam.

Further, the frame includes a main frame and a secondary frame that are detachably connected to each other, the first accommodating unit is surroundingly formed by at least a part of the main frame, and the second accommodating unit is surroundingly formed by at least a part of the main frame and at least a part of the secondary frame, the supplementary part is accommodated in the second accommodating unit, and disposition of the secondary frame facilitates replacement of the supplementary part of the moderator.

Preferably, a material of the main frame is an aluminum alloy, has relatively good mechanical properties, and after being activated by the neutrons, generates a radioactive isotope that has a short half-life.

Preferably, a material of the secondary frame is a carbon fiber composite material, after being activated by the neutrons, generates a radioactive isotope that has a short half-life, and brings low radiation.

Preferably, the main frame includes a first wall, a second wall, and a first transverse plate connecting the first wall and the second wall, wherein the first wall and the second wall are sequentially disposed along a direction of the neutron beam and are circumferentially closed surrounding the main axis, the first transverse plate extends perpendicular to the direction of the neutron beam, the first wall is provided to mount a transmitting tube of the accelerator, the second wall surroundingly forms the first accommodating unit, and a radial distance from the first wall to the main axis is less than a radial distance from the second wall to the main axis. The basic part of the moderator surrounds the target, so that the neutrons generated by the target may be effectively moderated in all directions, thereby further improving flux and beam quality of the neutrons.

Further, the main frame includes a third wall circumferentially closed surrounding a direction of the neutron beam, the radial distance from the second wall to the main axis is less than a radial distance from the third wall to the main axis, the frame further includes first and second side plates respectively disposed on two sides of the third wall along the direction of the neutron beam and connected to the third wall, and the secondary frame includes a second transverse plate disposed between the second wall and the second side plate along the direction of the neutron beam.

Preferably, the secondary frame further includes a fourth wall circumferentially closed surrounding the direction of the neutron beam and extending between the second transverse plate and the second side plate. The neutron capture therapy system further includes a collimator, the fourth wall forms a mounting portion and/or a beam exit of the collimator. The secondary frame made of carbon fibers is used in a direction of the beam exit, and compared with an aluminum alloy, the carbon fibers have a smaller activation degree, high strength and a specific moderating effect. The secondary frame also serves as the mounting portion of the collimator. The main frame further includes a radial separator disposed between the first side plate and the second transverse plate and extending from the first wall to the second wall or the third wall, the first wall, the second wall, the third wall, the first transverse plate, the second transverse plate, and the first side plate surroundingly form the second accommodating unit, the radial separator circumferentially divides the second accommodating unit into several sub-regions, the third wall, the fourth wall, the second transverse plate, and the second side plate surroundingly form a third accommodating unit, at least a part of the reflector/radiation shield is further disposed inside the second accommodating unit, and at least a part of the radiation shield is disposed inside the third accommodating unit, and materials of the first and second side plates are a lead-antimony alloy. Lead may further shield radiation, and in addition, the lead-antimony alloy has relatively high strength.

Preferably, the basic part is provided with a center hole in a first end face facing toward the first side plate, the center hole is provided to accommodate the transmitting tube of the accelerator and the target, and when the basic part is filled up, a first end face of the supplementary part close to the second side plate is flush with a second end face of the basic part close to the second side plate. Further, a shielding plate is disposed adjacent to the second end face of the basic part. The shielding plate is a lead plate. Lead may absorb gamma rays released in the moderator. A thickness of the shielding plate in the direction of the neutron beam is less than or equal to 5 cm, so that the neutrons passing through the moderator are not reflected. When the number of the pieces of the basic part is reduced, the positioning member is disposed adjacent to the shielding plate. The stopping member is disposed adjacent to the second transverse plate, and the stopping member is detachably connected to the main frame and/or secondary frame, to facilitate adjustment and replacement of the basic part of the moderator.

Another aspect of the present invention provide a neutron capture therapy system, including a neutron generating device and a beam shaping assembly, where neutrons generated by the neutron generating device form a neutron beam, the neutron beam defines a main axis, and the beam shaping assembly is provided to adjust beam quality of the neutron beam, where the beam shaping assembly includes a moderator, a reflector, and a radiation shield, the moderator is configured to moderate the neutrons generated from the neutron generating device to an epithermal neutron energy region, the reflector surrounds the moderator and directs deviating neutrons back to the main axis to enhance intensity of an epithermal neutron beam, and the radiation shield is provided to shield leaking neutrons and photons so as to reduce dose to normal tissues in a non-irradiation area; and the beam shaping assembly further includes a frame accommodating the moderator, and the frame includes a main frame and a secondary frame that are detachably connected to each other. The frame positions and supports the moderator, so that flux and quality of the neutron source may be improved. The main frame and the secondary frame are detachably connected to each other, to facilitate replacement of the moderator.

Further, a material of the main frame is an aluminum alloy, has relatively good mechanical properties, and after being activated by the neutrons, generates a radioactive isotope that has a short half-life.

Further, a material of the secondary frame is a carbon fiber composite material, after being activated by the neutrons, generates a radioactive isotope that has a short half-life, and brings low radiation.

Further, the moderator is adjustable, and the frame includes a positioning member and a stopping member for fixing the moderator. Preferably, half-lives of radioactive isotopes generated after materials of the positioning member and the stopping member are activated by the neutrons are less than 7 days. Preferably, the materials of the positioning member and stopping member are an aluminum alloy, a titanium alloy, a lead-antimony alloy, a cobalt-free steel, carbon fibers, PEEK, or a high molecular polymer. The positioning member may conveniently adjust a size of the moderator, thereby adjusting flux of the neutron beam, and after the adjustment, the stopping member may quickly and conveniently implement encapsulation of the moderator.

Further, the moderator includes a basic part and a supplementary part, a material of the basic part is different from a material of the supplementary part, the frame forms at least one accommodating unit, the accommodating unit includes a first accommodating unit and a second accommodating unit that are adjacent to each other, the basic part is accommodated in the first accommodating unit. The supplementary part may lower manufacturing costs of the moderator without exerting relatively large impact on quality of the beam. Preferably, a material of the basic part includes at least one of $D_2O$, Al, $AlF_3$, $MgF_2$, $CaF_2$, LiF, $Li_2CO_3$, or $Al_2O_3$, has a cross section for principally acting with fast neutrons but hardly acting with epithermal neutrons, and has a relatively good moderating effect. The basic part contains Li-6, and the basic part also serves as a thermal neutron absorber. Preferably, a material of the supplementary part includes at least one of Zn, Mg, Al, Pb, Ti, La, Zr, Bi, or C. Selecting a material that is relatively easy to obtain as the material of the supplementary part may lower manufacturing costs of the moderator while producing a specific neutron moderating effect without exerting relatively large impact on quality of the beam.

Further, the basic part is composed of pieces and adjustable, when a number of the pieces of the basic part is reduced, the positioning member is disposed inside the first accommodating unit for supplementation, and the stopping member is provide to fix the basic part. The positioning member and the stopping member may conveniently adjust the basic part of the moderator.

Further, the first accommodating unit is surroundingly formed by at least a part of the main frame, and the second accommodating unit is surroundingly formed by at least a part of the main frame and at least a part of the secondary frame, the supplementary part is accommodated in the second accommodating unit, and disposition of the secondary frame facilitates replacement of the supplementary part of the moderator.

The frame of the beam shaping assembly of the neutron capture therapy system according to the present invention positions and supports the moderator, so that flux and quality of the neutron source may be improved.

Further areas of applicability will become apparent from the description provided herein. It should be understood that the description and specific examples are intended for purposes of illustration only and are not intended to limit the scope of the present disclosure.

BRIEF DESCRIPTION OF THE DRAWINGS

The accompanying drawings illustrate one or more embodiments of the disclosure and together with the written description, serve to explain the principles of the disclosure. Wherever possible, the same reference numbers are used throughout the drawings to refer to the same or like elements of an embodiment.

DETAILED DESCRIPTION OF THE DISCLOSURE

Embodiments of the present invention are further described below in detail with reference to the accompanying drawings, to enable a person skilled in the art to implement the present invention with reference to the text of the specification.

Figure 1:
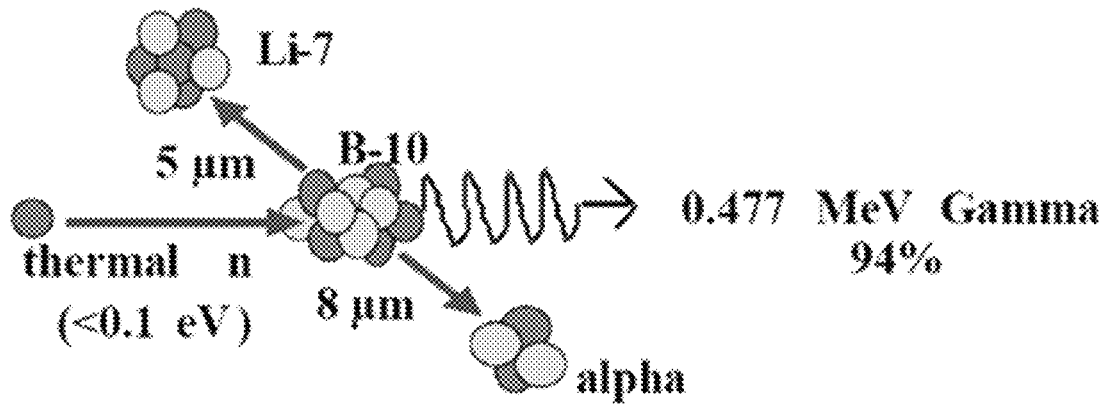
FIG. 1 is a schematic diagram of a boron neutron capture reaction.
Figure 2:
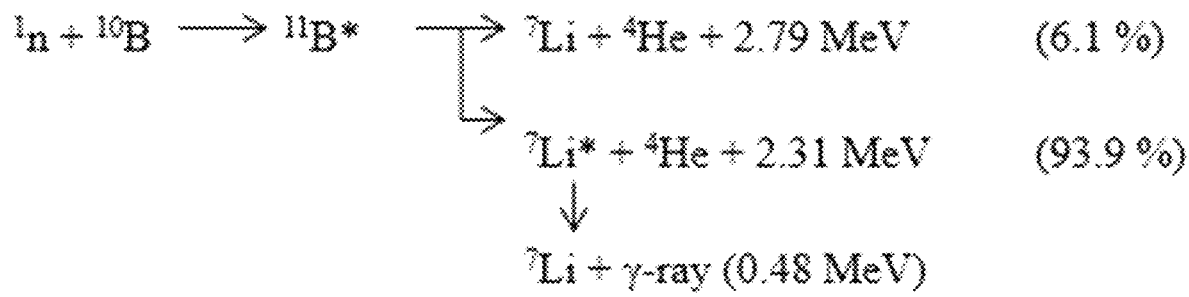
FIG. 2 shows a nuclear reaction equation of $^{10}B(n,\alpha)^7Li$ neutron capture.
Figure 3:
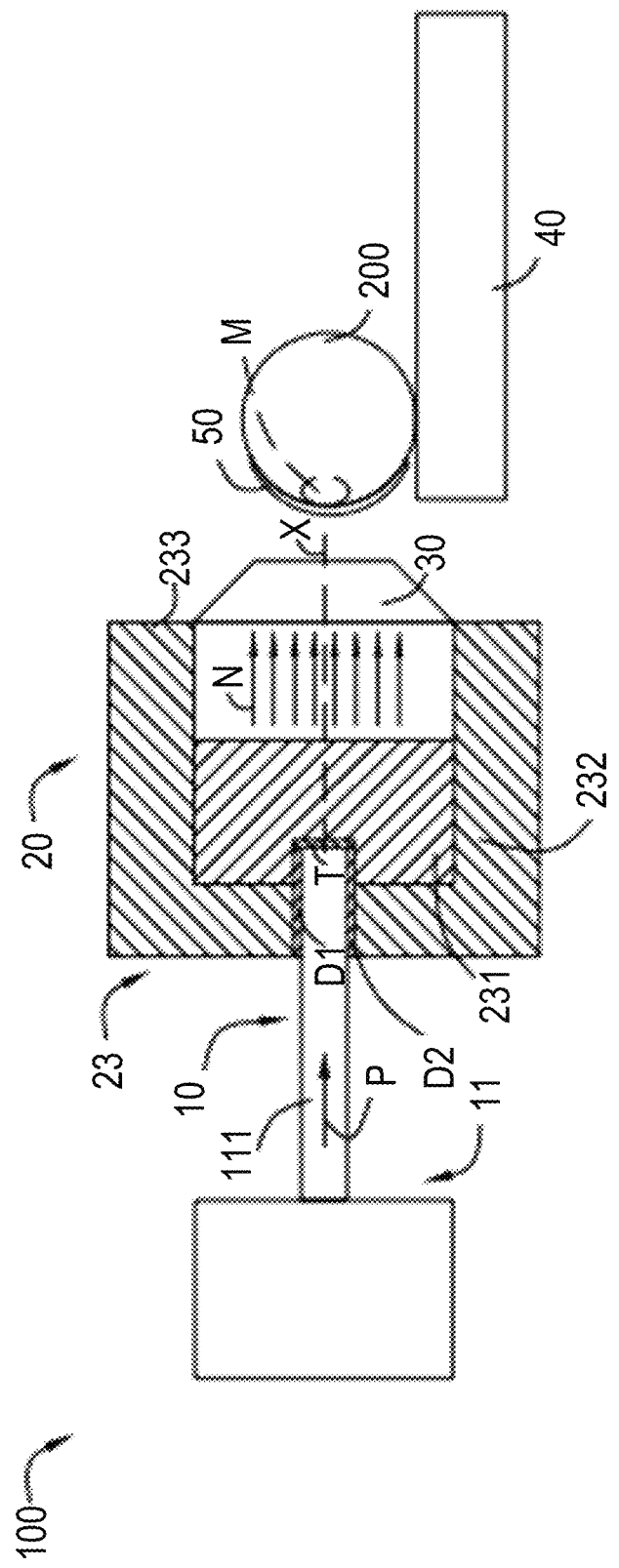
FIG. 3 is a schematic diagram of a neutron capture therapy system according to an embodiment of the present disclosure.

As shown in FIG. 3, a neutron capture therapy system in this embodiment is preferably a boron neutron capture therapy system 100, which includes a neutron generating device 10, a beam shaping assembly 20, a collimator 30, and a treatment table 40. The neutron generating device 10 includes an accelerator 11 and a target T, and the accelerator 11 accelerates charged particles (such as protons, deuterons, etc.) to generate a charged particle beam P such as a proton beam, and the charged particle beam P irradiates the target T and interacts with the target T to generate neutrons which form a neutron beam N, the neutron beam define a main axis X, and the target T is a metal target. The neutron beam N direction described below with reference to the accompanying drawings does not represent the actual neutron motion direction, but the overall motion trend direction of the neutron beam N. Suitable nuclear reactions are always determined according to such characteristics as desired neutron yield and energy, available accelerated charged particle energy and current and materialization of the metal target, among which the most discussed two are $^7Li$ (p, n) $^7Be$ and $^9Be$ (p, n) $^9B$ and both are endothermic reaction. Their energy thresholds are 1.881 MeV and 2.055 MeV respectively. Epithermal neutrons at a keV energy level are considered ideal neutron sources for BNCT. Theoretically, bombardment with lithium target using protons with energy slightly higher than the thresholds may produce neutrons relatively low in energy, so the neutrons may be used clinically without many moderations. However, Li (lithium) and Be (beryllium) and protons of threshold energy exhibit not high action cross section. In order to produce sufficient neutron fluxes, high-energy protons are usually selected to trigger the nuclear reactions. The target, considered perfect, is supposed to have the advantages of high neutron yield, a produced neutron energy distribution near the epithermal neutron energy range (see details thereinafter), little strong-penetration radiation, safety, low cost, easy accessibility, high temperature resistance etc. But in reality, no nuclear reactions may satisfy all requests. However, well known by those skilled in the art, the target materials may be made of other metals besides Li or Be, for example, tantalum (Ta) or tungsten (W) or their alloys. The accelerator 11 may be a linear accelerator, a cyclotron, a synchrotron, a synchrocyclotron.

Only mixed radiation fields are produced from BNCT neutron sources, that is, beams include neutrons and photons having energies from low to high. As for BNCT in the depth of tumors, except the epithermal neutrons, the more the residual quantity of radiation ray is, the higher the proportion of nonselective dose deposition in the normal tissue is. Therefore, radiation causing unnecessary dose should be lowered down as much as possible. Besides air beam quality factors, dose is calculated using a human head tissue prosthesis in order to understand dose distribution of the neutrons in the human body. The prosthesis beam quality factors are later used as design reference to the neutron beams, which is elaborated hereinafter.

The International Atomic Energy Agency (IAEA) has given five suggestions on the air beam quality factors for the clinical BNCT neutron sources. The suggestions may be used for differentiating the neutron sources and as reference for selecting neutron production pathways and designing the beam shaping assembly, and are shown as follows:

Epithermal neutron flux >1×10$^9$n/cm$^2$s
Fast neutron contamination <2×10$^{-13}$ Gy-cm$^2$/n
Photon contamination <2×10$^{-13}$ Gy-cm$^2$/n
Thermal to epithermal neutron flux ratio <0.05
Epithermal neutron current to flux ratio >0.7

Note: the epithermal neutron energy range is between 0.5 eV and 40 keV, the thermal neutron energy range is lower than 0.5 eV, and the fast neutron energy range is higher than 40 keV.

1. Epithermal Neutron Flux

The epithermal neutron flux and the concentration of the boronated pharmaceuticals at the tumor site codetermine clinical therapy time. If the boronated pharmaceuticals at the tumor site are high enough in concentration, the epithermal neutron flux may be reduced. On the contrary, if the concentration of the boronated pharmaceuticals in the tumors is at a low level, it is required that the epithermal neutrons in the high epithermal neutron flux should provide enough doses to the tumors. The given standard on the epithermal neutron flux from IAEA is more than 10$^9$ epithermal neutrons per square centimeter per second. In this flux of neutron beams, therapy time may be approximately controlled shorter than an hour with the boronated pharmaceuticals. Thus, except that patients are well positioned and feel more comfortable in shorter therapy time, and limited residence time of the boronated pharmaceuticals in the tumors may be effectively utilized.

2. Fast Neutron Contamination

Unnecessary dose on the normal tissue produced by fast neutrons is considered as contamination. The dose exhibits positive correlation to neutron energy, hence, the quantity of the fast neutrons in the neutron beams should be reduced to the greatest extent. Dose of the fast neutrons per unit epithermal neutron flux is defined as the fast neutron contamination, and according to IAEA, it is supposed to be less than 2*10$^{-13}$ Gy-cm$^2$/n.

3. Photon Contamination (Gamma-Ray Contamination)

Gamma-ray long-range penetration radiation will selectively result in dose deposit of all tissues in beam paths, so that lowering the quantity of gamma-ray is also the exclusive requirement in neutron beam design. Gamma-ray dose accompanied per unit epithermal neutron flux is defined as gamma-ray contamination which is suggested being less than 2*10$^{-13}$ Gy-cm$^2$/n according to IAEA.

4. Thermal to Epithermal Neutron Flux Ratio

The thermal neutrons are so fast in rate of decay and poor in penetration that they leave most of energy in skin tissue after entering the body. Except for skin tumors like melanocytoma, the thermal neutrons serve as neutron sources of BNCT, in other cases like brain tumors, the quantity of the thermal neutrons has to be lowered. The thermal to epithermal neutron flux ratio is recommended at lower than 0.05 in accordance with IAEA.

5. Epithermal Neutron Current to Flux Ratio

The epithermal neutron current to flux ratio stands for beam direction, the higher the ratio is, the better the forward direction of the neutron beams is, and the neutron beams in the better forward direction may reduce dose surrounding the normal tissue resulted from neutron scattering. In addition, treatable depth as well as positioning posture is improved. The epithermal neutron current to flux ratio is better of larger than 0.7 according to IAEA.

The prosthesis beam quality factors are deduced by virtue of the dose distribution in the tissue obtained by the prosthesis according to a dose-depth curve of the normal tissue and the tumors. The three parameters as follows may be used for comparing different neutron beam therapy effects.

1. Advantage Depth

Tumor dose is equal to the depth of the maximum dose of the normal tissue. Dose of the tumor cells at a position behind the depth is less than the maximum dose of the normal tissue, that is, boron neutron capture loses its advantages. The advantage depth indicates penetrability of neutron beams. Calculated in cm, the larger the advantage depth is, the larger the treatable tumor depth is.

2. Advantage Depth Dose Rate

The advantage depth dose rate is the tumor dose rate of the advantage depth and also equal to the maximum dose rate of the normal tissue. It may have effects on length of the therapy time as the total dose on the normal tissue is a factor capable of influencing the total dose given to the tumors. The higher it is, the shorter the irradiation time for giving a certain dose on the tumors is, calculated by cGy/mA-min.

3. Advantage Ratio

The average dose ratio received by the tumors and the normal tissue from the brain surface to the advantage depth is referred to as an advantage ratio. The average ratio may be calculated using dose-depth curvilinear integral. The higher the advantage ratio is, the better the therapy effect of the neutron beams is.

To provide comparison reference to design of the beam shaping assembly, we also provide the following parameters for evaluating expression advantages and disadvantages of the neutron beams in the embodiments of the present disclosure except the air beam quality factors of IAEA and the abovementioned parameters.

1. Irradiation time ≤30 min (proton current for accelerator is 10 mA)
2. 30.0 RBE-Gy treatable depth ≥7 cm
3. The maximum tumor dose ≥60.0 RBE-Gy
4. The maximum dose of normal brain tissue ≤12.5 RBE-Gy
5. The maximum skin dose ≤11.0 RBE-Gy Note: RBE stands for relative biological effectiveness. Since photons and neutrons express different biological effectiveness, the dose above should be multiplied with RBE of different tissues to obtain equivalent dose.

The neutron beam N generated by the neutron generating device 10 sequentially passes through the beam shaping assembly 20 and the collimator 30 and then irradiates to the patient 200 on the treatment table 40. The beam shaping assembly 20 is capable of adjusting the beam quality of the neutron beam N generated by the neutron generating device 10, and the collimator 30 is provided to concentrate the neutron beam N, so that the neutron beam N has higher targeting during the treatment process. The beam shaping assembly 20 further includes a frame 21 and a main part 23, at least part of the main part 23 is filled within the frame 21, the frame 21 forms supporting to the main part 23, which may prevent the deformation and damage of the material and affect the target replacing and quality of the beam. The main part 23 includes a moderator 231, a reflector 232, a radiation shield 233. The neutrons generated by the neutron generating device 10 have a wide spectrum of energy, and in addition to epithermal neutrons to meet treatment needs, it is desirable to reduce other types of neutrons and photons as much as possible to avoid injury to operators or patients. Therefore, the neutrons coming out of the neutron generating device 10 need to pass through the moderator 231 to adjust the energy of fast neutrons therein to the epithermal neutron energy region. The moderator 231 is made of a material having a cross section for principally acting with fast neutrons but hardly acting with epithermal neutrons, such as includes at least one of $D_2O$, $AlF_3$, Fluental, $CaF_2$, $Li_2CO_3$, $MgF_2$ and $Al_2O_3$. The reflector 232 surrounds the moderator 231, and reflects the neutrons diffused through the moderator 231 back to the neutron beam N to improve the utilization of the neutrons, and is made of a material having high neutron reflection ability, such as includes at least one of Pb and Ni. The radiation shield 233 is provided to shield leaking neutrons and photons so as to reduce dose of a normal tissue not exposed to irradiation. The material of the radiation shield 233 includes at least one of a photon shielding material and a neutron shielding material, such as a photon shielding material lead (Pb) and a neutron shielding material polyethylene (PE). It should be appreciated that the main part may have other configurations as long as the epithermal neutron beam required for treatment may be obtained. The target T is disposed between the accelerator 11 and the beam shaping assembly 20, and the accelerator 11 has a transmitting tube 111 that transmits the charged particle beam P. In this embodiment, the transmitting tube 111 penetrates into the beam shaping assembly 20 in the direction of the charged particle beam P, and sequentially passes through the moderator 231 and the reflector 232. The target T is arranged into the moderator 231 and located at the end of the transmitting tube 111 to obtain a better neutron beam quality. In this embodiment, first and second cooling pipes D1 and D2 are disposed between the transmitting tube 111 and the moderator 231, and between the transmitting tube 111 and the reflector 232, and one end of the first and second cooling pipes D1, D2 is respectively connected to the cooling inlet IN (not shown in FIGS.) and the cooling outlet OUT (not shown in FIGS.) of the target T, and the other ends are connected to an external cooling source (not shown in FIGS.). It should be understood that the first and second cooling tubes may also be disposed into the beam shaping assembly in other ways, and may also be omitted when the target is placed outside the beam shaping assembly.

Figure 4:
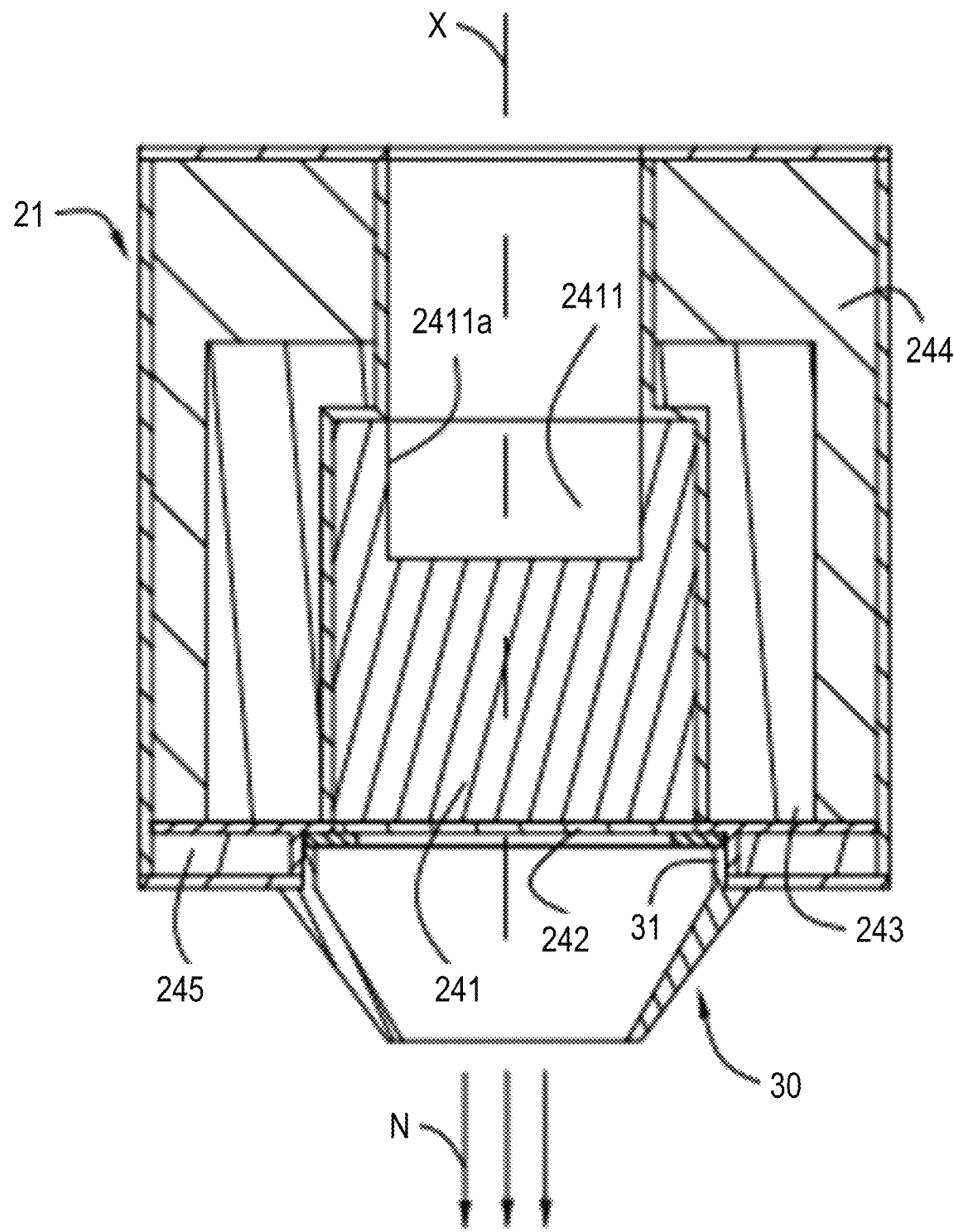
FIG. 4 is a schematic diagram of a beam shaping assembly and a collimator of a neutron capture therapy system according to an embodiment of the present disclosure.
Figure 5:
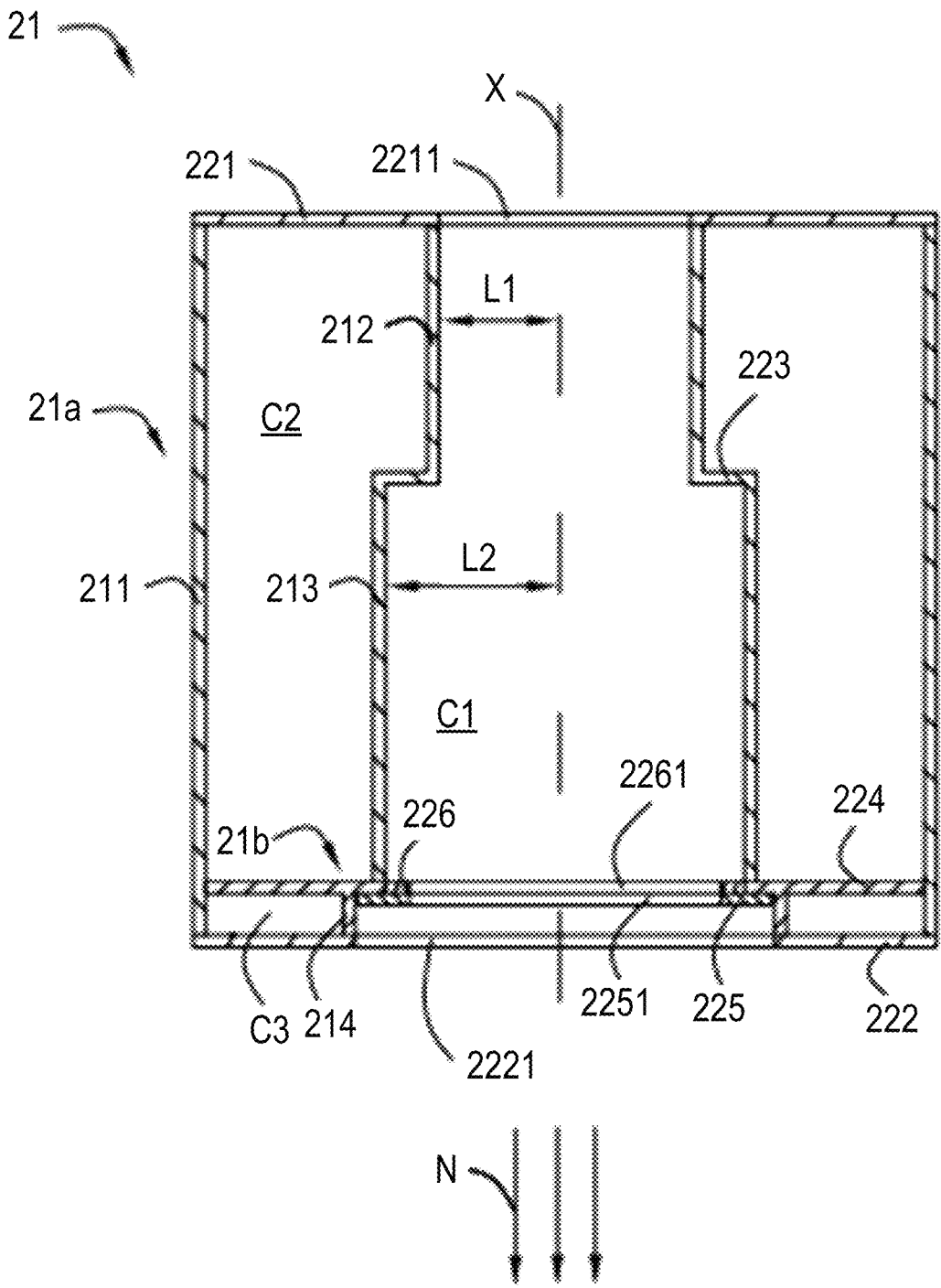
FIG. 5 is a schematic diagram of a frame in FIG. 4.

Referring to FIG. 4 and FIG. 5, the frame 21 includes a first wall 211 circumferentially closed surrounding the main axis X and first and second side plates 221, 222 respectively disposed on two sides of the first wall 211 along a direction of the neutron beam N and connected to the first wall 211. The first side plate 221 is provided with a hole 2211 for the transmitting tube 111 to pass through. The second side plate 222 is provided with a hole 2221 that forms a beam exit. An accommodating portion C of the moderator is formed among the first wall 211 and the first and second side plates 221, 222. At least a part of the reflector and/or radiation shield is also disposed inside the accommodating portion C. The accommodating portion C includes at least one accommodating unit C1-C3 (described in detail below). Each accommodating unit C1-C3 accommodates at least one of the moderator 231, the reflector 232, and the radiation shield 233. The at least one accommodating unit accommodates all of at least two of the moderator, the reflector, and the radiation shield or accommodates all of at least two different materials. The moderator 231 includes a basic part and a supplementary part, and the basic part and the supplementary part are respectively accommodated in different accommodating units. It may be understood that the first and second side plates may alternatively not be disposed, and the first wall surroundingly forms an accommodating portion.

The frame 21 further includes a first transverse plate 223 disposed between the first and the second side plates 221, 222 in the direction of the neutron beam N, a second wall 212 circumferentially closed surrounding the main axis X and extending between the first transverse plate 223 and the first side plate 221, and a third wall 213 circumferentially closed surrounding the main axis X and extending from the first transverse plate 223 to the second side plate 222. The second wall 212 is radially closer to the main axis X than the third wall 213, the third wall 213 is radially located between the first wall 211 and the second wall 212, and the first transverse plate 223 extends between the second wall 212 and the third wall 213. An inner surface of the second wall 212 and a side wall of the hole 2211 in the first side plate 221 are on a same surface, and the second wall 212 forms a mounting portion of the transmitting tube 111, the first and second cooling tubes D1, D2, and the like. It may be understood that the first transverse plate may extend to the first wall.

The frame 21 further includes a second transverse plate 224 disposed between the third wall 213 and the second side plate 222 in the direction of the neutron beam N, a fourth wall 214 circumferentially closed surrounding the main axis X and extending between the second transverse plate 224 and the second side plate 222, and the third transverse plate 225 disposed between the second transverse plate 224 and the second side plate 222 and adjacent to the second transverse plate 224. The second transverse plate 224 extends from the first wall 211 to an inner side of the third wall 213. The fourth wall 214 is radially located between the first wall 211 and the third wall 213, and an inner surface of the fourth wall 214 and the side wall of the hole 2221 in the second side plate 222 are on a same surface, the fourth wall 214 and the hole 2221 in the second side plate 222 jointly form a beam exit, and a hole 2251 for the neutron beam N to pass through is formed in the third transverse plate 225. The third wall 213 is radially located between the fourth wall 214 and an inner wall of the hole 2251 in the third transverse plate 225, and an outer wall of the third transverse plate 225 is located between an inner surface of the fourth wall 214 and an inner surface of the third wall 213.

In this embodiment, cross sections of the first, second, third, and fourth walls perpendicular to the direction of the main axis X are all circular rings surrounding the main axis X, and the first, second, third, and fourth walls extend parallel to the main axis X. The side plates and the transverse plates are all flat plates extending perpendicular to the main axis X. It may be understood that there may be other settings. For example, an extending direction is inclined to the main axis. The frame may further include a plurality of walls circumferentially closed surrounding the main axis X and a plurality of transverse plates disposed between the walls, and may be further provided to accommodate or support other parts of the beam shaping assembly.

A region that is from the first transverse plate 223 to the third transverse plate 225 in the direction of the neutron beam N and that is surrounded by the third wall 213 forms a first accommodating unit C1. A second accommodating unit C2 is formed among the first wall 211, the second wall 212, the third wall 213, the first side plate 221, the first transverse plate 223, and the second transverse plate 224. A third accommodating unit C3 is formed among the first wall 211, the fourth wall 214, the second transverse plate 224, and the second side plate 222.

A magnesium fluoride block 241 is disposed inside the first accommodating unit C1 as the basic part of the moderator 231. The magnesium fluoride block 241 contains Li-6 and may also be used as a thermal neutron absorber. The magnesium fluoride block 241 is cylindrical as a whole and is provided with a center hole 2411 on an end face thereof facing toward the first side plate 221. The center hole 2411 is provided to accommodate the transmitting tube 111, the first and second cooling tubes D1, D2, the target T, and the like. The center hole 2411 is a cylindrical hole, a side wall 2411a of the center hole and the inner surface of the second wall 212 are on a same surface. A radial distance L1 from the second wall 212 to the main axis X is less than a radial distance L2 from the third wall 213 to the main axis X, so that the basic part of the moderator 231 surrounds the target T. Therefore, the neutrons generated by the target T may be effectively moderated in all directions, thereby further improving flux and beam quality of the neutrons. A lead plate 242 is disposed between the magnesium fluoride block 241 and the third transverse plate 225. The lead plate 242 serves as a photon shield. Lead may absorb gamma rays released in the moderator. In addition, the thickness of the lead plate 242 in the direction of the neutron beam N is less than or equal to 5 cm, so that the neutrons passing through the moderator are not reflected. It may be understood that, there may be other settings. For example, the magnesium fluoride block 241 does not contain Li-6, and instead, the thermal neutron absorber made of Li-6 is separately disposed between the magnesium fluoride block 241 and the third transverse plate 225. The lead plate may also be omitted.

An aluminum alloy block 243 and a lead block 244 are disposed inside the second accommodating unit C2. The aluminum alloy block 243 has surfaces in contact with the second wall 212, the third wall 213, and the first transverse plate 223, so that the aluminum alloy block 243, as the supplementary part of the moderator 231, surrounds the basic part of the moderator 231 disposed inside the first accommodating unit C1. The aluminum alloy block 243, as the supplementary part of the moderator 231, may lower manufacturing costs of the moderator without exerting relatively large impact on quality of the beam. APE block 245 in a corresponding shape is disposed inside the third accommodating unit C3. In this embodiment, the radiation shield 233 includes a neutron shield and a photon shield. The PE block 245 serves as the neutron shield. The lead block 244 serves as both the reflector 232 and the photon shield. It may be understood that the PE block may further be disposed inside the second accommodating unit C2 as neutron shield.

The magnesium fluoride block 241 is composed of pieces, which is convenient for quality control and adjusting beam intensity by increasing or decreasing the number of the pieces. In the embodiment shown in FIG. 4, when the magnesium fluoride block 241 is filled up, the magnesium fluoride block 241 is flush with an end face of the aluminum alloy block 243 close to the second side plate 222, and the lead plate 242 is disposed adjacent to an end face of the magnesium fluoride block 241 close to the second side plate 222 and is in contact with the third transverse plate 225. When the number of tiles of magnesium fluoride block 241 is reduced, a positioning ring 226 (shown in FIG. 5) is disposed between the lead plate 242 and the third transverse plate 225 for corresponding supplementation. It may be understood that the positioning ring 226 may also be disposed between the magnesium fluoride block 241 and the lead plate 242. The third transverse plate 225 serves as a stopping ring, and the positioning ring 226 is also provided with a hole 2261 that has a hole diameter as that of the stopping ring and that is used for the neutron beam N to pass through. The positioning rings 226 of different thicknesses may be disposed in advance to position the magnesium fluoride block 241. Materials of the positioning ring 226 and the stopping ring (the third transverse plate 225) are carbon fibers, and after being activated by the neutrons, generate a radioactive isotope that has a relatively short half-life. It may be understood that the positioning ring and the stopping ring may alternatively be replaced with positioning and stopping members in other forms. The positioning member may conveniently adjust a size of the moderator, thereby adjusting flux of the neutron beam, and after the adjustment, the stopping member may quickly and conveniently implement encapsulation of the moderator.

It may be understood that in this embodiment, PE that serves as the neutron shield may be replaced with another neutron shielding material; lead that serves as the photon shield may be replaced with another photon shielding material; lead that serves as the reflector may be replaced with another material having a strong neutron reflecting capability; magnesium fluoride that serves as the basic part of the moderator may be replaced with another material having a cross section for principally acting with fast neutrons but hardly acting with epithermal neutrons; Li-6 that serves as the thermal neutron absorber may be replaced with another material having a cross section for principally acting with thermal neutrons; and an aluminum alloy that serves as the supplementary part of the moderator may be replaced with a material including at least one of Zn, Mg, Al, Pb, Ti, La, Zr, Bi, Si, or C. Selecting a material that is relatively easy to obtain as the material of the supplementary part may lower manufacturing costs of the moderator while producing a specific neutron moderating effect without exerting relatively large impact on quality of the beam.

Figure 6:
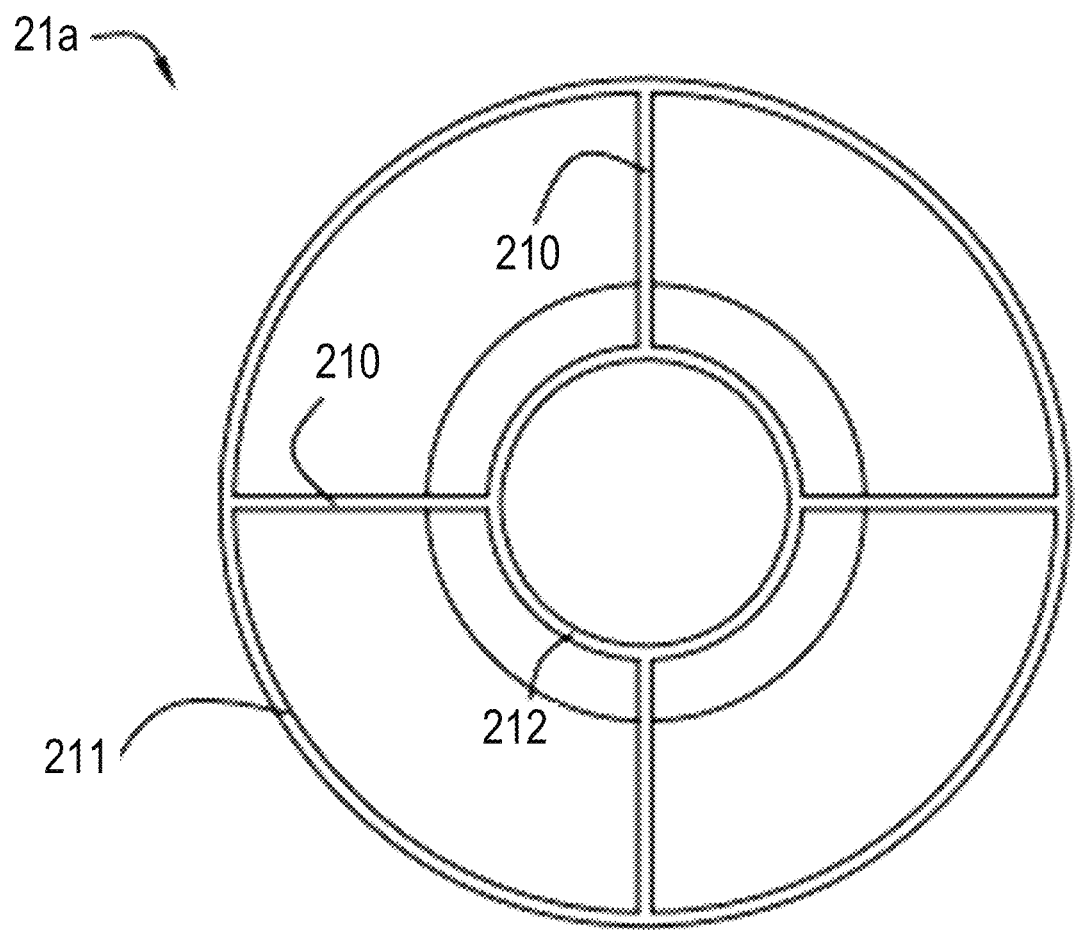
FIG. 6 is a schematic diagram of a main frame in FIG. 5 viewed from a direction of a neutron beam N.
Figure 7:
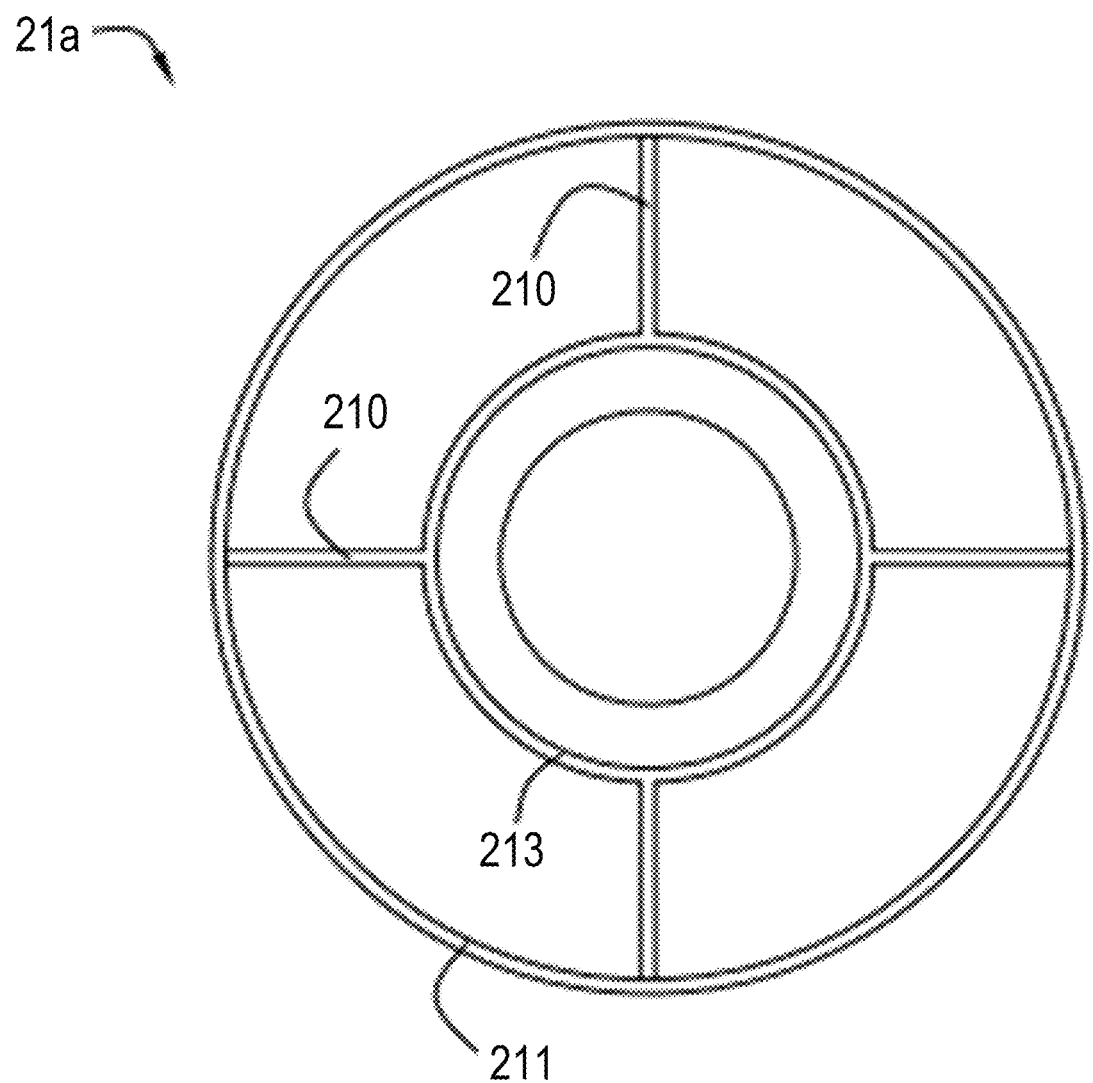
FIG. 7 is a schematic diagram of the main frame in FIG. 5 viewed from a direction opposite to the direction of the neutron beam N.

Referring to FIG. 6 and FIG. 7, a radial separator 210 is further disposed in the frame 21, and a plane on which the radial separator 210 is located extends through the main axis X, to circumferentially divide the second accommodating unit C2 into at least two sub-regions, so that the lead block and the aluminum alloy block disposed inside the second accommodating unit C2 are both circumferentially divided into at least two submodules. In this embodiment, the radial separator 210 is disposed between the first side plate 221 and the second transverse plate 224, and extends from the first wall 211 to the second wall 212 or the third wall 213. The radial separators 210 are four flat plates evenly and circumferentially distributed. It may be understood that there may be another number or another arrangement, or no radial separator disposed.

In this embodiment, the radial separator 210, the first transverse plate 223, and the first, second, and third walls 211-213 are integrated, serve as a main frame 21a, are made of an aluminum alloy, have good mechanical properties, after being activated by the neutrons, generate a radioactive isotope that has a short half-life, and may be integrally formed by using a casting process and a supporting mold. A wood mold or an aluminum mold is selected as a template, and red sand or resin sand may be selected as a sand core. A common method in the industry may be selected as a specific process. Because casting is accompanied by a demolding slope, according to the design and requirements on beam quality, complete removal is required in machining. The structural form and the casting process endow the frame structure with advantages of good integrity, high rigidity, and a high bearing capacity. In consideration of limitations of machining tools and stress concentration on right-angle edges, all corners are rounded. Alternatively, a plate is rolled and welded, or an aluminum alloy cylinder is first forged, and then, the cylinder is machined and shaped. The second transverse plate 224 and the fourth wall 214 are integrated as a secondary frame 21b made of a carbon fiber composite material. A common method in the industry may be selected as a specific process. An aluminum alloy and a carbon fiber composite material, after being activated by the neutrons, generate radioactive isotopes that have short half-lives, and bring low radiation. Carbon fibers are used in a direction of the beam exit and compared with the aluminum alloy, have a smaller activation degree and higher strength, and also have a specific moderating effect. The main frame 21a and the secondary frame 21b are connected by a bolt, and a first screw hole is uniformly machined on the end face of the third wall 213 facing toward the second side plate 222. A first through hole is uniformly machined at a position corresponding to the first screw hole on the second transverse plate 224. The bolt passes through the first through hole and is connected to the first screw hole. In consideration of mounting of the stopping ring (the third transverse plate 225), a second screw hole is uniformly reserved on the end face of the third wall 213 facing toward the second side plate 222. Positions of the second screw hole and the first screw hole are different. A second through hole is reserved at a position corresponding to the second screw hole on the second transverse plate 224. A third through hole is machined in the stopping ring (the third transverse plate 225). A position of the third through hole corresponds to the second through hole. The bolt passes through the third through hole and the second through hole in sequence, and is connected to the second screw hole, so that the stopping ring (the third transverse plate 225) is fixed by the bolt to the main frame 21a. It may be understood that the stopping ring may also be fixed to the secondary frame. In addition, a fourth through hole is machined in the stopping ring (the third transverse plate 225). The fourth through hole has a position that corresponds to the first through hole and a hole diameter that is slightly greater than a maximum radial size of the head of the bot that connects the main frame 21a and the secondary frame 21b, and is provided to accommodate the head of the bolt. It may be understood that the fourth through hole may alternatively be a blind hole. In consideration of assembly of the bolt, a hole diameter of the first through hole is slightly greater than a hole diameter of the first screw hole, and hole diameters of the second and third through holes are greater than a hole diameter of the second screw hole. Numbers of the first screw holes, the first through holes, the second screw holes, the second through holes, and the third through holes only need to satisfy connection strength. It may be understood that the secondary frame, the positioning ring, and the stopping ring may alternatively be omitted.

The first and second side plates 221, 222 are made of a lead-antimony alloy. Lead may further shield radiation. In addition, the lead-antimony alloy has relatively strong strength. The first and second side plates 221, 222 are both connected to the main frame by bolts. The third screw holes are uniformly machined on end faces of an inner wall of the main frame 21a facing toward the first and second side plates. and the fourth through holes are uniformly machined at positions corresponding to the third screw holes on the first and second side plates 221, 222. In consideration of assembly of the bots, the hole diameter of the fourth through hole is slightly greater than the hole diameter of the third screw hole. Numbers of the third screw holes and the fourth through hole only need to satisfy connection strength.

It may be understood that in this embodiment, materials of the main frame, the secondary frame, the side plates, the positioning ring, and the stopping ring only need to have specific strength and after being activated by the neutrons, generate radioactive isotopes that have short half-lives (for example, less than 7 days). The material of the main frame only needs to have properties satisfying the requirement of supporting the beam shaping assembly, and may be, for example, an aluminum alloy, a titanium alloy, a lead-antimony alloy, a cobalt-free steel, carbon fibers, PEEK, or a high molecular polymer. Another connecting manner may alternatively be adopted provided that the stopping ring and the frame are detachably connected to each other, to facilitate adjustment and replacement of the basic part of the moderator. The secondary frame and the side plates are connected to the main frame detachably or undetachably. When a detachable connection is adopted, respective parts of the main body may be conveniently replaced. In this embodiment, the frame and the main body of the beam shaping assembly may alternatively have another construction manner.

The collimator 30 is disposed at the back of the beam exit, and an epithermal neutron beam from the collimator 30 irradiates the patient 200, and after passing through a shallow normal tissue, is moderated into thermal neutrons and reaches a tumor cell M. With reference to FIG. 4, in this embodiment, the collimator 30 and the secondary frame 21b are fixed through a threaded connection, and the fourth wall 214 of the secondary frame 21b forms a mounting portion of the collimator 30. The collimator 30 includes a flange 31 surrounding the main axis X on an end portion close to the beam shaping assembly 20. An outer wall of the flange 31 includes an external thread (not shown in the figure), and an inner wall of the fourth wall 214 is provided with an internal thread (not shown in the figure) that matches the external thread. It may be understood that the collimator 30 may alternatively be fixed in another connecting manner. The collimator 30 may alternatively be omitted or replaced with another structure. The neutron beam out of the beam exit directly irradiates the patient 200. In this embodiment, a radiation shielding device 50 is further disposed between the patient 200 and the beam exit to shield normal tissue of the irradiated subject from irradiation by the beam from the beam exit. It should be understood that the radiation shielding device 50 may not be disposed.

The term 'cylindrical' or 'cylindrical section' referred in the embodiment of the present disclosure is an element with the contour in a substantially unchanged trend from one side to the other side along the illustrated direction. One of contour lines may be a line segment, like a corresponding one of the cylinder, or may be a high-curvature arc approximate to the line segment, like a corresponding one of a sphere with high curvature. The integral surface of the contour may be continuously connected or not if the surface of the cylinder or the high-curvature sphere is provided with many protrusions and grooves.

Although the illustrative embodiments of the present invention have been described above in order to enable those skilled in the art to understand the present invention, it should be understood that the present invention is not to be limited the scope of the embodiments. For those skilled in the art, as long as various changes are within the spirit and scope as defined in the present invention and the appended claims, these changes are obvious and within the scope of protection claimed by the present invention.

What is claimed is:

1. A neutron capture therapy system, comprising:
   a neutron generating device comprising:
   an accelerator, and
   a target,
   wherein a charged particle beam generated by an acceleration of the accelerator interacts with the target to generate neutrons, the neutrons form a neutron beam, the neutron beam defines a main axis; and
   a beam shaping assembly comprising:
   a moderator configured to moderate neutrons generated from the target to an epithermal neutron energy range,
   a reflector surrounding the moderator and directing deviating neutrons back to the main axis to enhance an intensity of an epithermal neutron beam, and
   a radiation shield provided to shield leaking neutrons and photons so as to reduce a dose to normal tissues in a non-irradiation area, and
   a frame accommodating the moderator.

2. The neutron capture therapy system according to claim 1, wherein the moderator is adjustable, and the frame comprises a positioning member and a stopping member for fixing the moderator.

3. The neutron capture therapy system according to claim 2, wherein the positioning member and the stopping member comprise materials which, when activated by the neutrons, generate radioactive isotopes, and wherein half-lives of the radioactive isotopes are less than 7 days.

4. The neutron capture therapy system according to claim 2, wherein the positioning member and the stopping member comprise materials, and wherein the materials comprise an aluminum alloy, a titanium alloy, a lead-antimony alloy, a cobalt-free steel, carbon fibers, PEEK, or a high molecular polymer.

5. The neutron capture therapy system according to claim 2, wherein the moderator comprises a basic part and a supplementary part, a material of the basic part is different from a material of the supplementary part, the frame forms at least one accommodating unit, the at least one accommodating unit comprises a first accommodating unit and a second accommodating unit that are adjacent to each other, the basic part is accommodated in the first accommodating unit and comprises pieces and adjustable, when a number of the pieces of the basic part is reduced, the positioning member is disposed inside the first accommodating unit for a supplementation, and the stopping member is configured to fix the basic part.

6. The neutron capture therapy system according to claim 5, wherein the basic part comprises a material, and wherein the material comprises at least one of $D_2O$, Al, $AlF_3$, $MgF_2$, $CaF_2$, LiF, $Li_2CO_3$, or $Al_2O_3$, the basic part contains Li-6, and the basic part also serves as a thermal neutron absorber.

7. The neutron capture therapy system according to claim 5, wherein the supplementary part comprises a material, and wherein the material comprises at least one of Zn, Mg, Al, Pb, Ti, La, Zr, Bi, or C.

8. The neutron capture therapy system according to claim 5, wherein the frame comprises a main frame and a secondary frame that are detachably connected to each other, the first accommodating unit is surroundingly formed by at least a part of the main frame, and the second accommodating unit is surroundingly formed by at least a part of the main frame and at least a part of the secondary frame, and the supplementary part is accommodated in the second accommodating unit.

9. The neutron capture therapy system according to claim 8, wherein the main frame comprises a material and the secondary frame comprises a material, and wherein the material of the main frame is an aluminum alloy, and the material of the secondary frame is a carbon fiber composite material.

10. The neutron capture therapy system according to claim 8, wherein the main frame comprises a first wall, a second wall, and a first transverse plate connecting the first wall and the second wall, wherein the first wall and the second wall are sequentially disposed along a direction of the neutron beam and are circumferentially closed surrounding the main axis, the first transverse plate extends perpendicular to the direction of the neutron beam, the first wall is provided to mount a transmitting tube of the accelerator, the second wall surroundingly forms the first accommodating unit, and a radial distance from the first wall to the main axis is less than a radial distance from the second wall to the main axis.

11. The neutron capture therapy system according to claim 10, wherein the main frame further comprises a third wall circumferentially closed surrounding the direction of the neutron beam, the radial distance from the second wall to the main axis is less than a radial distance from the third wall to the main axis, the frame further comprises a first side plate and a second side plate respectively disposed on two sides of the third wall along the direction of the neutron beam and connected to the third wall, and the secondary frame comprises a second transverse plate disposed between the second wall and the second side plate along the direction of the neutron beam.

12. The neutron capture therapy system according to claim 11, further comprising a collimator, wherein the secondary frame further comprises a fourth wall circumferentially closed surrounding the direction of the neutron beam and extending between the second transverse plate and the second side plate, the fourth wall forms a mounting portion and/or a beam exit of the collimator, the main frame further comprises a radial separator disposed between the first side plate and the second transverse plate and extending from the first wall to the second wall or the third wall, the first wall, the second wall, the third wall, the first transverse plate, the second transverse plate, and the first side plate surroundingly form the second accommodating unit, the radial separator circumferentially divides the second accommodating unit into several sub-regions, the third wall, the fourth wall, the second transverse plate, and the second side plate surroundingly form a third accommodating unit, at least a part of the reflector or the radiation shield is further disposed inside the second accommodating unit, and at least a part of the radiation shield is disposed inside the third accommodating unit, and materials of the first side plate and the second side plate are a lead-antimony alloy.

13. The neutron capture therapy system according to claim 11, wherein the basic part comprises a center hole in a first end face facing toward the first side plate, the center hole is configured to accommodate the transmitting tube of the accelerator and the target, and when the basic part is filled up, a first end face of the supplementary part close to the second side plate is flush with a second end face of the basic part close to the second side plate.

14. The neutron capture therapy system according to claim 13, further comprising a shielding plate, wherein the shielding plate is disposed adjacent to the second end face of the basic part, the shielding plate is a lead plate, a thickness of the shielding plate in the direction of the neutron beam is less than or equal to 5 cm, when the number of the pieces of the basic part is reduced, the positioning member is disposed adjacent to the shielding plate, the stopping member is disposed adjacent to the second transverse plate, and the stopping member is detachably connected to the main frame and/or the secondary frame.

15. A neutron capture therapy system, comprising:
a neutron generating device, comprising a target, wherein a charged particle beam interacts with the target to generate neutrons, the neutrons form a neutron beam, and the neutron beam defines a main axis; and
a beam shaping assembly provided to adjust a beam quality of the neutron beam, wherein the beam shaping assembly comprises:
a moderator configured to moderate neutrons generated from the target to an epithermal neutron energy range,
a reflector surrounding the moderator and directing deviating neutrons back to the main axis to enhance an intensity of an epithermal neutron beam,
a radiation shield provided to shield leaking neutrons and photons so as to reduce a dose to normal tissues in a non-irradiation area, and
a frame accommodating the moderator, wherein the frame comprises a main frame and a secondary frame that are detachably connected to each other.

16. The neutron capture therapy system according to claim 15, wherein the main frame comprises a material and the secondary frame comprises a material, and wherein the material of the main frame is an aluminum alloy, and the material of the secondary frame is a carbon fiber composite material.

17. The neutron capture therapy system according to claim 15, wherein the moderator is adjustable, and the frame further comprises a positioning member and a stopping member for fixing the moderator.

18. The neutron capture therapy system according to claim 17, wherein the moderator comprises a basic part and a supplementary part, a material of the basic part is different from a material of the supplementary part, the frame forms at least one accommodating unit, the at least one accommodating unit comprises a first accommodating unit and a second accommodating unit that are adjacent to each other, the basic part is accommodated in the first accommodating unit.

19. The neutron capture therapy system according to claim 18, wherein the basic part comprises pieces and adjustable, when a number of the pieces of the basic part is reduced, the positioning member is disposed inside the first accommodating unit for a supplementation, and the stopping member is configured to fix the basic part.

20. The neutron capture therapy system according to claim 18, wherein the first accommodating unit is surroundingly formed by at least a part of the main frame, and the second accommodating unit is surroundingly formed by at least a part of the main frame and at least a part of the secondary frame, and the supplementary part is accommodated in the second accommodating unit.

* * * * *